United States Patent
Diorio et al.

(10) Patent No.: US 11,324,699 B2
(45) Date of Patent: *May 10, 2022

(54) LIPID MULTIPARTICULATE FORMULATIONS

(71) Applicant: Capsugel Belgium NV, Bornem (BE)

(72) Inventors: Christopher Diorio, Campbell Hall, NY (US); John Lokhnauth, Fair Lawn, NJ (US); Chang Lee, Bethesda, MD (US)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/523,711

(22) PCT Filed: Nov. 24, 2015

(86) PCT No.: PCT/EP2015/077428
§ 371 (c)(1),
(2) Date: May 2, 2017

(87) PCT Pub. No.: WO2016/087261
PCT Pub. Date: Jun. 9, 2016

(65) Prior Publication Data
US 2017/0354599 A1    Dec. 14, 2017

Related U.S. Application Data

(60) Provisional application No. 62/087,766, filed on Dec. 4, 2014.

(51) Int. Cl.
*A61K 9/14* (2006.01)
*A61K 9/51* (2006.01)
(Continued)

(52) U.S. Cl.
CPC .............. *A61K 9/145* (2013.01); *A61K 9/143* (2013.01); *A61K 9/148* (2013.01); *A61K 9/5123* (2013.01); *A61K 31/045* (2013.01); *A61K 31/122* (2013.01)

(58) Field of Classification Search
CPC ....... A61K 9/145; A61K 9/5123; A61K 9/148
See application file for complete search history.

(56) References Cited

U.S. PATENT DOCUMENTS 5,380,535 A    1/1995  Geyer
5,635,200 A    6/1997  Douglas et al.
(Continued)

FOREIGN PATENT DOCUMENTS

EP    1030687    8/2000
EP    1469848    10/2004
(Continued)

OTHER PUBLICATIONS

Anand et al., "Bioavailability of Curcumin: Problems and Promises," *Molecular Pharmaceutics*, 4(6):807-818 (Nov.- Dec. 2007).
(Continued)

*Primary Examiner* — Lakshmi S Channavajjala
(74) *Attorney, Agent, or Firm* — Klarquist Sparkman, LLP

(57) ABSTRACT

Disclosed are various embodiments of lipid multiparticulate compositions comprising at least one active agent, a low flow point excipient, and a high flow point excipient.

14 Claims, 1 Drawing Sheet

(51) Int. Cl.
A61K 31/122 (2006.01)
A61K 31/045 (2006.01)

(56) References Cited

U.S. PATENT DOCUMENTS

| | | | |
|---|---|---|---|
| 5,869,098 A | 2/1999 | Misra et al. | |
| 5,976,577 A | 11/1999 | Green et al. | |
| 6,413,549 B2 | 7/2002 | Green et al. | |
| 6,509,040 B1 | 1/2003 | Murray et al. | |
| 6,572,892 B1 | 6/2003 | Loulalen et al. | |
| 6,680,071 B1 | 1/2004 | Johnson et al. | |
| 7,235,260 B2 | 6/2007 | Crew et al. | |
| 7,625,507 B2 | 12/2009 | Ray et al. | |
| 7,887,844 B2 | 2/2011 | Appel et al. | |
| 10,166,187 B2* | 1/2019 | Diorio | A61K 9/1694 |
| 2004/0265375 A1 | 12/2004 | Platteeuw et al. | |
| 2005/0013834 A1* | 1/2005 | Ljusberg | A61K 9/0065 |
| | | | 424/400 |
| 2005/0123615 A1 | 6/2005 | Ray et al. | |
| 2006/0141053 A1 | 6/2006 | Menjoge et al. | |
| 2008/0096853 A1* | 4/2008 | van Amelsvoort | A23L 29/10 |
| | | | 514/182 |
| 2008/0200452 A1 | 8/2008 | Obermeier et al. | |
| 2009/0131373 A1 | 5/2009 | Gopro et al. | |
| 2009/0142401 A1* | 6/2009 | Appel | A61K 9/1617 |
| | | | 424/489 |
| 2009/0324703 A1 | 12/2009 | Frautschy et al. | |
| 2010/0221298 A1* | 9/2010 | Ioualalen | A61K 31/167 |
| | | | 424/401 |
| 2011/0306539 A1 | 12/2011 | Shen | |
| 2013/0017239 A1* | 1/2013 | Viladot Petit | A61K 8/0283 |
| | | | 424/401 |
| 2016/0000714 A1* | 1/2016 | Diorio | A61K 9/5063 |
| | | | 424/502 |
| 2017/0112762 A1 | 4/2017 | Sivert et al. | |

FOREIGN PATENT DOCUMENTS

| | | |
|---|---|---|
| EP | 1691787 | 8/2006 |
| EP | 1827382 | 9/2007 |
| EP | 2044929 | 4/2009 |
| EP | 2964243 | 1/2016 |
| EP | 3226845 | 10/2017 |
| WO | WO99/02140 | 1/1999 |
| WO | WO99/65448 | 12/1999 |
| WO | WO2004/084856 | 10/2004 |
| WO | WO2004/084865 | 10/2004 |
| WO | WO2005/053654 | 6/2005 |
| WO | WO2006/070141 | 7/2006 |
| WO | WO2007/101551 | 9/2007 |
| WO | WO2010/143199 | 12/2010 |
| WO | WO2012/023142 | 2/2012 |
| WO | WO2013/183062 | 12/2013 |
| WO | WO2014/135967 | 9/2014 |
| WO | WO2015/189726 | 12/2015 |
| WO | WO2016/087261 | 6/2016 |

OTHER PUBLICATIONS

Cuomo et al., "Comparative Absorption of a Standardized Curcuminoid Mixture and Its Lecithin Formulation," *Journal of Natural Products,* 74(4):664-669 (Apr. 2011).
Dadhaniya, p et al., "Safety assessment of a solid lipid curcumin particle preparation: Acute and subchronic toxicity studies," *Food and Chemical Toxicology,* vol. 49, No. 8, pp. 1834-1842 (May 2011).
Gomes, G. V. L et al., "Characterization and Shelf Life of β-Carotene Loaded Solid Lipid Microparticles Produced With Stearic Acid and Sunflower Oil," *Braz. Arch. Biol. Technol.,* 56(4):663-671 (Jul./Aug. 2013).
International Preliminary Report on Patentability for PCT/IB2014/000463 (dated Sep. 17. 2015).
International Preliminary Report on Patentability for PCT/IB2015/053568 (dated Dec. 22, 2016).
International Search Report and Written Opinion for PCT/IB2014/000463 (dated Jun. 18, 2014).
International Search Report and Written Opinion for PCT/IB2015/053568 (dated Sep. 14, 2015).
International Search Report and Written Opinion for PCT/EP2015/077428, dated Jan. 26, 2016.
Kakkar et al., "Exploring solid lipid nanoparticles to enhance the oral bioavailability of curcumin," *Mol. Nutr. Food Res.,* 55(3):495-503 (Mar. 2011).
Marcyzlo et al., "Comparison of systemic availability of curcumin with that of curcumin formulated with phosphatidylcholine," *Cancer Chemother. Pharmacol.,* 60(2):171-177 (Jul. 2007).
Office Action from the United States Patent and Trademark Office for U.S. Appl. No. 14/771,117, dated Sep. 23, 2016.
Passerini, N. et al., "Solid lipid microparticles produced by spray congealing: Influence of the atomizer on microparticle characteristics and mathematical modeling of the drug release," *Journal of Pharmaceutical Sciences,* 99(2):916–931 (Feb. 2010).
Pawar et al., "Novel lipid based oral formulation of curcumin: Development and optimization by design of experiments approach," *International Journal of Pharmaceutics,* 436(1-2):617-623 (Jul. 2012).
Restriction Requirement Action from the United States Patent and Trademark Office for U.S. Appl. No. 14/771,117, dated May 6, 2016.
Solanki, K., Incorporation of Curcumin in Lipid Based Delivery Systems and Assessment of its Bioaccessibility, Thesis submitted to the Graduate School-New Brunswick Rutgers, The State University of New Jersey, 91 pages (Oct. 2012).
Gattefosse (2010). "Compritol® 888 ATO". Retrieved on May 10, 2017. Retrieved from the internet <URL:http://www.gattefosse.com/en/applications/compritol-888-ato.html>.
International Preliminary Report on Patentability for PCT/EP2015/077428 (dated Jun. 15, 2017).
Office Action from the United States Patent and Trademark Office for U.S. Appl. No. 15/313,512, dated May 19, 2017.
Examination Report issued by European Patent Office for EPC Application No. 15730266.2 dated Aug. 29, 2019.
Final Office Action from the United States Patent and Trademark Office for U.S. Appl. No. 14/771,117, dated May 19, 2017.
Non-Final Office Action from the Untied Statement Patent and Trademark Office for U.S. Appl. No. 15/313,512, dated Nov. 15, 2019.
Rosiaux et al., "Solid lipid excipients—matrix agents for sustained drug delivery," *Journal of Controlled Release,* 188:18-30, (Jun. 2014).
Weiner et al., "Dosage forms: lipid excipients," Encyclopedia of Pharmaceutical Technology, Third Edition, vol. 2, ed. Swarbrick, pp. 975-987, 2007.
Chauhan et al., "Preparation and Characterization of Etoricoxib Solid Dispersions Using Lipid Carriers by Spray Drying Technique," *AAPS PharmSciTech,* 6(3):E405-E412 (Oct. 2005).
Office Action from the European Office Action for European Patent Application No. 15798436.0, dated Aug. 20, 2020.
Extended European Search Report from the European Patent Office for European Patent Application No. 20184393.5, dated Dec. 2, 2020.

* cited by examiner

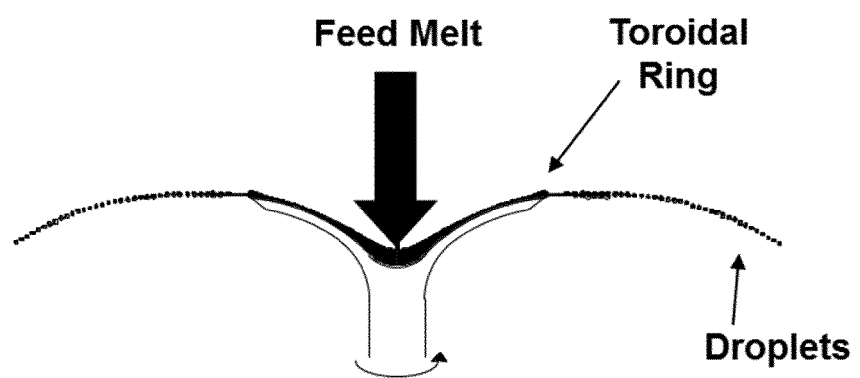

LIPID MULTIPARTICULATE FORMULATIONS

CROSS REFERENCE TO RELATED APPLICATIONS

This is the U.S. National Stage of International Application No. PCT/EP2015/077428, filed Nov. 24, 2015, which was published in English under PCT Article 21(2). which in turn claims the benefit of U.S. Provisional Application No. 62/087,766, filed Dec. 4, 2014. The provisional application is incorporated herein in its entirety.

FIELD

Disclosed are lipid multiparticulate compositions comprising an active agent, a low flow point excipient, and a high flow point excipient.

BACKGROUND

Solid compositions of lipid multiparticulates (LMPs) are known. See for example EP1030687, U.S. Pat. No. 6,572,892, EP1827382, U.S. Pat. Nos. 7,235,260, 7,887,844, EP1691787, U.S. Pat. No. 7,625,507.

SUMMARY

Disclosed are compositions comprising an active agent, at least one low flow point excipient, and least one high flow point excipient, wherein the composition comprises a plurality of particles that are solid at ambient temperature, have a generally spherical shape, and have a mean diameter ranging from 40 μm to 3000 μm.

In one embodiment the composition comprises a plurality of particles that are solid at ambient temperature, have a mean diameter ranging from 40 μm to 3000 μm, said particles comprising at least one active agent, and a matrix, wherein said matrix comprises at least one low flow point excipient and at least one high flow point excipient. In certain embodiments the composition has a mass ratio of said at least one low flow point excipient and said at least one high flow point excipient is at least 2:1, or at least 4:1, or at least 15:1. In some embodiments the composition comprises from 1 wt % to 60 wt % of the active agent. In some embodiments of the composition the high flow point excipient comprises at least 2 wt % of the composition. Certain embodiments of the composition further comprise a dispersing agent. In some embodiments the composition comprises from 0.01 wt % to 20 wt % of a dispersing agent. In certain embodiments the composition further comprises an antioxidant, with some embodiments having the from 0.01 wt % to 20 wt % antioxidant in the composition.

Some embodiments of the disclosed compositions further comprise a flow aid. In some such embodiments the flow aid comprises 0.01 wt % to 5 wt % of the composition. Also disclosed are embodiments of a composition comprising a plurality of particles that are solid at ambient temperature, have a mean diameter ranging from 40 μm to 3000 μm, said particles comprising at least one active agent, and a matrix, wherein said matrix comprises at least one low flow point excipient, at least one high flow point excipient and wherein the composition has an in vivo AUC value, wherein the AUC value divided by the amount dosed is at least 1.25-fold an AUC value of a control dosage form divided by the amount dosed.

In some embodiments the active agent is a carotenoid, such as lutein, astaxanthin, zeaxanthin, alpha-carotene, beta-carotene, cryptoxanthin, lycopene, and mixtures thereof.

Also disclosed are processes for making the disclosed compositions. In one such embodiment the process for making a composition comprises forming a molten mixture comprising at least one active agent, a low flow point excipient, and a high flow point excipient; directing the molten mixture to a spinning disk atomizer to form droplets; cooling the droplets to form solid particles, and collecting the particles.

DETAILED DESCRIPTION

The present disclosure relates to lipid multiparticulate (LMP) formulations comprising an active agent, a low flow point excipient, and a high flow point excipient. The combination of the formulation components that are not active comprise the matrix. In certain embodiments the matrix comprises or consists of a low flow point excipient and a high flow point excipient. The multiparticulates are in the form of a plurality of generally spherical particles that are solid at ambient temperature. Various embodiments are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions

As used in the present disclosure, the following words, phrases, and symbols are generally intended to have the meanings as set forth below, except to the extent that the context in which they are used indicates otherwise.

As used herein, "optional" or "optionally" means that the subsequently described material, event or circumstance may or may not be present or occur, and that the description includes instances where the material, event or circumstance is present or occurs and instances in which it does not.

As used herein, "w/w %" and "wt %" means by weight as a percentage of the total weight or relative to another component in the composition.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

The term excipient is meant any pharmaceutically acceptable ingredient that is included in the formulation that is not the one or more active agents. The term glyceride is meant a fatty acid ester of glycerol. By "fatty acid ester of glycerol" is meant mono, di, and tri esters of glycerides. Glycerides also include glycerol esters that have both fatty acid and poly alkyl oxide esters.

As used herein, the term "flow point" is the temperature at which any portion of the mixture becomes sufficiently fluid that the mixture, as a whole, may be atomized. Generally, a mixture is sufficiently fluid for atomization when the viscosity of the molten mixture is less than 20,000 cp, or less than 15,000 cp, or less than 10,000 cp, less than 5000 cp, or even less than 1000 cp. The viscosity can be measured by controlled stress rheometer, which measures viscosity as a function of temperature, and may use either a shear-type or rotational rheometer. As used herein, melting point refers to the temperature that marks the midpoint of the transition from a solid crystalline or semi-crystalline state to a liquid state. As measured by DSC, the melting point is the temperature where upon heating the solid material, the maximum exothermic heat flow occurs. In general, melting point will be used in reference to relative pure single component materials such as some actives or essentially single component excipients (e.g. stearyl alcohol) and flow point will be used in reference to multi-component materials or mixtures.

The term "ambient temperature" refers to a temperature of 20° C.

Unless otherwise indicated, "capsule" means a container suitable for enclosing solids or liquids, and includes empty capsule shells and components thereof such as caps and bodies that may be assembled together to form the capsule.

Unless otherwise indicated, "dosage form" refers to a solid composition comprising an active ingredient.

Active Agents

Embodiments of the disclosed compositions include at least one active agent. The compositions may contain one or more active agents. As used herein, by "active" or "active agent" is meant a drug, medicament, pharmaceutical, therapeutic agent, nutraceutical, or other compound that may be desired to be administered to the body. The active may be a "small molecule," generally having a molecular weight of 2000 Daltons or less. The active may also be a "biological active." Biological actives include proteins, antibodies, antibody fragments, peptides, oligonucleotides, vaccines, and various derivatives of such materials. In one embodiment, the active is a small molecule. In another embodiment, the active is a biological active. In still another embodiment, the active is a mixture of a small molecule and a biological active.

In one embodiment, the active is a carotenoid. Examples of carotenoids include lutein, astaxanthin, zeaxanthin, alpha-carotene, beta-carotene, cryptoxanthin, lycopene and mixtures thereof. In some embodiments, the carotenoid is obtained as an oil, typically an extract from a natural product, and may contain a variety of components. Those components that are structurally and functionally similar to lutein, astaxanthin and zeaxanthin are considered active agents. The remaining components comprise the active matrix and are considered excipients.

In some embodiments, the active agent is crystalline in the compositions. In other embodiments, the active agent is non-crystalline in the compositions. In still another embodiment, the active agent may comprise crystalline and non-crystalline regions in the compositions. In some embodiments, the active agent is at least 60 wt % crystalline. In other embodiments, the active agent is at least 75 wt %. In another embodiment, the active agent is at least 90 wt % crystalline. In other embodiments, the active may dissolve into the excipients prior to forming the LMPs. During the multiparticulate formation process, a portion of the crystalline active agent may dissolve into the molten mixture up to the active agent's solubility limit in the molten mixture at the processing conditions. When the molten mixture is cooled to form the multiparticulates, the multiparticulate will comprise particles of crystalline active agent encapsulated in a solid solution of excipient and the dissolved active agent.

Low Flow Point Excipients

The lipid multiparticulates include a low-flow point excipient. Low flow point excipients generally include fatty alcohols, fatty acids, fatty acid esters of glycols and poly glycols, fatty acid esters of polyglycerol and fatty acid esters of glycerol (glycerides) with flow points of less than 50° C. When the low flow point excipient is a relatively pure material, the melting point is also less than 50° C. A preferred class of low flow point excipients are low flow point glycerides. By "low flow point" excipient, such as a glyceride, is meant that the melting point of the excipient, such as a glyceride, is less than 50° C. In some embodiments, the low flow point glyceride has a melting point of less than 40° C. In some embodiments, the low-flow point excipient, such as glyceride, is a mixture of compounds, having a flow point of 50° C. or less. In some embodiments, the low-flow point excipient, such as glyceride, has a flow point of 40° C. or less. In some embodiments, the low-flow point glyceride has a low flow point of 30° C. or less.

Exemplary low flow point glycerides include polyglycolized glycerides, such as some of the Gelucire products manufactured by Gattefosse, such as Gelucire® 43/01 having a nominal melting point of 43° C. Mixtures of low flow point glycerides are also effective, such as mixtures of Gelucire® 43/01 ($C_{10}$-$C_{18}$ triglycerides), Gelucire® 50/13 (stearoyl polyoxylglycerides), Gelucire® 44/14 (lauroyl macrogol-32 glycerides), and mixtures thereof. Other glycerides may also be used, such as fatty acid esters of glycols and poly glycols, and fatty acid esters of polyglycerols.

A function of the low flow point excipient is to ensure that at least a significant portion of the formulation matrix softens when ingested orally by a patient in need of therapy, at the temperature of the GI tract (about 37° C. for humans). This allows the formulation to break down by digestion in the gastro-intestinal (GI) tract, and ultimately to disperse in the GI tract to promote dissolution and absorption of the active. In certain embodiments the low flow point excipient provides a significant portion of the formulation matrix to be present in a non-crystalline liquid or amorphous state when ingested and softened in the GI tract.

Exemplary low flow point fatty alcohols include myristyl alcohol (Tm 38° C.), lauryl alcohol (Tm 23° C.) and capric alcohol (Tm 7° C.).

Exemplary low flow point fatty acids include lauric acid (Tm 44° C.) and oleic acid (Tm 16° C.).

High Flow Point Excipients

The lipid multi particulates include a high-flow point excipient. By "high flow point" excipient is meant an excipient that has a flow point 50° C. or more. High flow point excipients may also have a melting point above 50° C. High flow point excipients generally include fatty alcohols, fatty acids, fatty acid esters of glycols and poly glycols, fatty acid esters of polyglycerol, fatty acid esters of glycerol (glycerides), waxes, polar waxes and other materials with flow points of greater than 50° C. A preferred class of high flow point excipients are "high flow point glycerides". By high flow point glyceride is meant that the flow point or melting point of the glyceride is 50° C. or more. In some embodiments, the high flow point glyceride has a melting point of 60° C. or more. In some embodiments, the high-melting point glyceride is a mixture of compounds, having a flow point of 50° C. or more. In some embodiments, the high-flow point glyceride has a flow point of 60° C. or more. In some embodiments, the high flow point glyceride has a flow point of 70° C. or more.

Exemplary high flow point glycerides include glycerol behenate, glycerol dibehenate, glycerol palmitate, hydrogenated castor oil, and mixtures thereof. Often, the high flow point glyceride is a mixture of compounds that are formulated into a product and sold under a variety of trade names.

Exemplary high flow point and high melt point fatty alcohols include stearyl alcohol (Tm 58° C.) and behenyl alcohol (Tm 71° C.).

Exemplary high flow point and high melt point fatty acids include palmitic acid (Tm 63° C.) and stearic acid (Tm>70° C.).

Exemplary waxes include paraffin wax, beeswax, candelilla wax, carnauba wax, and mixtures thereof.

A function of the high flow point excipient is to aid in the manufacturability of the LMPs by enabling the LMP to congeal at a lower temperature to obtain solid particles during the melt-spray-congeal processing. In certain embodiments the high flow point excipient aids the physical stability of the LMP formulation. In most embodiments, the high flow point excipient is not appreciably digested in the GI tract.

Other Excipients Including Dispersing Agents, Antioxidants, and Flow Aids

In some embodiments, the LMPs include other excipients to improve the performance and chemical stability of the formulations. In some embodiments, a dispersing agent is included in the LMPs. Exemplary dispersing agents include lecithin, glycerin monostearate, ethylene glycol palmitostearate, aluminum oxide, polyethylene alky ethers, sorbitan esters, and mixtures thereof.

In one embodiment, the LMPs include an antioxidant to maintain chemical stability of the active agent. Exemplary antioxidants include vitamin E, tocopheryl polyethylene glycol succinate (TPGS), rosemary extract, ascorbic acid, asorbyl palmitate, butylated hydroxyanisole (BHA), butylated hydroxytoluene (BHT), and mixtures and combinations thereof.

In some embodiments, a flow aid is used to improve the flow properties of the LMPs. Exemplary flow aids also known as glidants include calcium silicate, cab-o-sil, silicon dioxide, calcium phosphate tribasic, colloidal silicone dioxide, magnesium silicate, magnesium trisilicate, starch, talc, and other flow aids.

Physical Properties of the LMPs

The LMPs are a plurality of particles that are solid at ambient temperature and are generally spherical in shape, having a size ranging from a mean diameter of 40 µm to 3000 µm, or even 50 µm to 1000 µm, or even 100 µm to 300 µm. In general, the LMPs comprising active and all excipients that make up the matrix have a flow point above 25° C. In some embodiments, the flow point is above 30° C. or 35° C. or 40° C. In some embodiments, the flow point of the LMP composition is less than 50° C. or less than 40° C. By generally spherical is meant that while most particles are essentially spherical, they do not necessarily form "perfect" spheres. Such particle variations in spherical shapes are known to those persons of ordinary skill in the art of melt-spray-congeal processing and similar particulate forming methods. To measure the diameters of the particulates, there are several methods that can be used, including laser diffraction, optical microscopy, and/or SEM.

LMPs are advantageous active agent forms because they are amenable for use in scaling dosage forms according to the weight of an individual animal, including humans, in need of treatment by simply scaling the mass of particles in the dosage form to comport with the animal's weight. They are further advantageous since they allow the incorporation of a large quantity of active into a simple dosage form such as a capsule. Multiparticulates also have numerous therapeutic advantages over other dosage forms, especially when taken orally, including (1) improved dispersal in the gastrointestinal (GI) tract, (2) relatively rapid and reproducible passage from the stomach, (3) more uniform GI tract transit time, and (4) reduced inter- and intra-patient variability.

Level of Matrix Components

In one embodiment, the matrix composition comprises greater than 50 wt % of the low flow point excipient. In one embodiment, the matrix composition comprises at least 2 wt % of the high flow point excipient. In another embodiment, the matrix composition comprises less than 30 wt % of the high flow point excipient. In another embodiment the mass ratio of the low flow excipient to the high flow excipient is at least 20:1. In still another embodiment, the mass ratio of the low flow excipient to the high flow excipient is at least 15:1. In another embodiment, the mass ratio of the low flow excipient to the high flow excipient is at least 10:1. In another embodiment, the mass ratio of the low flow excipient to the high flow excipient is at least 4:1. In another embodiment, the mass ratio of the low flow excipient to the high flow excipient is at least 3:1. In another embodiment, the mass ratio of the low flow excipient to the high flow excipient is at least 2:1.

Compositions

The LMP formulations comprise an active agent, a low flow point excipient, and a high flow point excipient. In one embodiment, the active agent comprises from 1 wt % to 60 wt % of the LMP formulation. In another embodiment, the active agent comprises from 5 wt % to 25 wt % of the LMP formulation. In still another embodiment, the active agent comprises from 5 wt % to 20 wt % of the LMP formulation. In still another embodiment, the active agent comprises from 5 wt % to 15 wt % of the LMP formulation. In still another embodiment, the active agent comprises from 5 wt % to 10 wt % of the LMP formulation. When the active is present as a mixture or extract in an oil, only the active portion of the extract is considered the amount of active in the formulation. Thus, if a natural extract comprises 20 wt % of active carotenoids and 80 wt % inactive materials and the composition comprises 20 wt % of the natural extract, the composition comprises 4 wt % of the active agent.

The LMP formulations also comprise a low flow point excipient. In one embodiment, the LMP matrix is comprised of at least 10 wt % to 50 wt % of the low flow point excipient. In another embodiment, the LMP formulation is comprised of at least 50 wt % to 75 wt % of the low flow point excipient.

The LMP formulations also comprise a high flow point excipient. In one embodiment, the compositions comprise at least 2 wt % of the high flow point excipient. In another embodiment, the LMP matrix is comprised of 1 wt % to 30 wt % of the high flow point excipient. In still another embodiment, the LMP matrix is comprised of 2 wt % to 20 wt % of the high flow point excipient. In still another embodiment, the LMP matrix is comprised of 3 wt % to 15 wt % of the high flow point excipient.

The LMP formulations may also comprise a dispersing agent. In one embodiment, the LMP matrix is comprised of from 0 wt % to 20 wt %, such as from 0.01 wt % to 20 wt %, of a dispersing agent. In another embodiment, the LMP matrix is comprised of from 2 wt % to 10 wt % of a dispersing agent.

The LMP formulations may also comprise an antioxidant. In one embodiment, the LMP formulations comprise from 0 wt % to 20 wt %, such as from 0.01 wt % to 20 wt %, of an antioxidant. In one embodiment, the LMP formulations comprise from 1 wt % to 15 wt % of an antioxidant.

The LMP formulations may also comprise a flow aid. In one embodiment, the LMP formulations may comprise from 0 wt % to 5 wt %, such as from 0.01 wt % to 5 wt %, of a flow aid. In another embodiment, the LMP formulations may comprise from 0.5 wt % to 2 wt % of a flow aid.

In some embodiments, the compositions comprise an active agent, a low flow point excipient, and a high flow point excipient, where in the mass ratio of active agent is from 1 wt % to 60 wt %, the mass ratio of low flow point excipient from 10 wt % to 50 wt %, and the high flow point excipient ranges from 1 wt % to 30 wt % of the composition. In other embodiments, the mass ratio of active agent is from 5 wt % to 20 wt % of the composition, the mass ratio of the low flow point excipient is 50 wt % to 75 wt % of the composition, and the mass ratio of the high flow point excipient ranges from 2 wt % to 20 wt % of the composition. In still another embodiment, the mass ratio of active agent is from 5 wt % to 15 wt % of the composition, the mass ratio of the low flow point excipient is 50 wt % to 75 wt % of the composition, and the mass ratio of the high flow point excipient ranges from 3 wt % to 15 wt % of the composition.

In one embodiment, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a dispersing agent.

In some embodiments, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a dispersing agent.

In other embodiments, the compositions comprise from 5 wt % to 10 wt % of the active agent, from 60 wt % to 80 wt % of the low flow point excipient, from 2 wt % to 12 wt % of an antioxidant, from 2 wt % to 20 wt % of a high flow point excipient, and from 1 wt % to 10 wt % of a flow aid.

Processes for Making the Compositions

Exemplary processes include a "melt-spray-congeal" process. See, for example, U.S. Pat. Nos. 7,235,260, 7,887,844, EP1691787, U.S. Pat. No. 7,625,507.

A molten mixture is formed by mixing and heating the compositions previously described. Such compositions are comprised of an active agent, a low flow point excipient, and a high flow point excipient. "Molten mixture" means that the mixture of an active agent and matrix materials are sufficiently mixed and heated to fluidize the mixture sufficiently to allow it to be atomized into droplets. Generally, the mixture is molten in the sense that it will flow when subjected to one or more forces such as pressure, shear, and centrifugal force, such as that exerted by a centrifugal or spinning-disk atomizer.

Once the molten mixture has been formed, it is delivered to an atomizer that breaks the molten mixture into small droplets. Virtually any method can be used to deliver the molten mixture to the atomizer. In certain embodiments of the disclosed methods the molten mixture is delivered to the atomizer by use of pumps and/or various types of pneumatic devices such as pressurized vessels or piston pots or extruder. In certain embodiments the molten mixture is maintained at an elevated temperature during delivery to the atomizer to prevent its solidification and to keep it in a flowable state.

When a centrifugal atomizer (also known as rotary atomizers or spinning-disk atomizer) is used, the molten mixture is fed onto a rotating surface, where it spreads outward and flows by centrifugal force. The rotating surface may take several forms, examples of which include a flat disk, a cup, a vanned disk, and a slotted wheel. A preferred spinning disc design is shown in FIG. 1. The surface of the disk may also be heated to aid in atomization of the molten mixture or cooled to aid in the solidification of the LMPs. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk.

Once the molten mixture has been atomized, the droplets are congealed, typically by contact with a gas at a temperature below the solidification temperature of the composition. Typically, it is desirable that the droplets are congealed in less than 60 seconds, less than 10 seconds, or even in less than 1 second. In certain embodiments congealing at ambient temperature using an ambient temperature cooling medium, results in sufficiently rapid solidification of the droplets. However, as certain embodiments of the disclosed compositions are comprised of at least 50 wt % of a low flow point excipient, it is often preferred to utilize a cooling medium that is at a temperature that is at least 10° C. below ambient temperature. For some embodiments, it is preferred to utilize a cooling medium that is at least 20° C. below ambient temperature.

Dosage Forms

In one embodiment, the compositions of the invention are placed into a capsule for delivery by oral ingestion. Exemplary capsules include hard gelatin capsules, soft gelatin capsules, HPMC capsules as well as capsules made from other materials. The LMPs can also be suspended in a liquid such as an aqueous solution and then ingested. The LMPs may also be sprinkled on food and then ingested. The LMPs may also be mixed with solid excipients and then compressed into tablets.

Evaluation of Compositions

Bioavailability of the compositions can be tested in vivo in animals or humans using conventional methods for making such a determination. An in vivo test, such as a crossover study, may be used to determine whether a composition provides an enhanced active agent concentration in the blood (serum or plasma) versus time area under the curve (AUC) for a test subject, dosed with the composition relative to the active agent concentration in the blood versus time AUC for a test subject dosed with a control composition. The bioavailability is measured as the area under the curve (AUC) determined for each group. In vivo determinations of AUC can be made by plotting the serum or plasma concentration of active agent along the ordinate (y-axis) against time along the abscissa (x-axis). Generally, the values for AUC represent a number of values taken from all of the subjects in a patient test population and are, therefore, mean values averaged over the entire test population. By measuring the AUC for a population to which the test composition has been administered and comparing it with the AUC for the same population to which the control composition has been administered, the test composition can be evaluated. The determination of AUCs is a well-known procedure and is described, for example, in Welling, "Pharmacokinetics Processes and Mathematics," ACS Monograph 185 (1986).

In one embodiment, the AUC of the test composition divided by the amount dosed is at least 1.25-fold the AUC of the control composition divided by the amount dosed. In another embodiment, the AUC of the test composition divided by the amount dosed is at least 2-fold the AUC of the control composition divided by the amount dosed. In still another embodiment, the AUC of the test composition divided by the amount dosed is at least 2.5-fold the AUC of the control composition divided by the amount dosed. In still another embodiment, the AUC of the test composition divided by the amount dosed is at least 3-fold the AUC of the control composition divided by the amount dosed.

EXAMPLES

Example 1

The following components were formulated

| Function | Component | Amount (wt %) |
| --- | --- | --- |
| Active | Lutein (FloraGLO ® lutein 20%) | 8.3 |
| Low flow point excipient | $C_{10}$-$C_{18}$ Triglycerides (Gelucire ® 43/01) | 74.8 |
| Antioxidant | Vitamin E | 10.9 |
| High flow point excipient | Glyceryl behenate (Compritol ® E-ATO) | 5.0 |
| Flow aid | Calcium silicate | 1.0 |

Appropriate quantities of the low flow point excipient (Gelucire® 43/01), the high flow point excipient (Compritol® E-ATO), were melted in a water-jacketed tank at 75° C. and then mixed with the antioxidant (Vitamin E). After cooling the molten mixture to 55° C., the active (lutein) was added and mixed with the molten mixture. The molten mixture was then directed to a melt-spray congeal apparatus equipped with a spinning disk atomizer spinning at 2000 rpm. Droplets of the molten mixture formed and were congealed at 12° C. using air, which flowed through the collection chamber at 130 SCFM. The resulting particles were collected and the solid particles were blended with calcium silicate at the amount shown in Table 1. The LMPs had a generally spherical shape, and a mean particle size of 270 μm.

In Vivo Tests

In vivo tests were performed with 14 healthy adult humans under fed conditions, in a two-treatment, two-period, two-sequence, single dose, crossover, dosing 20 mg of Lutein (5 mg administering 4 capsules). The pharmacokinetic parameters are summarized in the following table. As a control, 20 mg of PreserVision® softgel capsules (5 mg/Softgel administering 4 capsules). The results are summarized in the following table.

| | Mean ± SD | |
| --- | --- | --- |
| Parameters (Units) | Example 1 | PreserVision ® |
| Cmax (ng/mL)/20 mg | 108 ± 57 | 64 ± 36 |
| $AUC_{0-72}$ (ng-hr/mL)/20 mg | 4290 ± 1896 | 1892 ± 1703 |

Example 1 showed a 1.87-fold increase in Cmax relative to the control dosage form, and an $AUC_{0-72}$ that was 3-fold higher than the control dosage form, all dosed at 20 mg per dose.

Example 2

The following components were formulated

| Function | Component | Amount (wt %) |
| --- | --- | --- |
| Active | AstaREAL ® Astaxanthin 10% oil | 10.05 |
| Low flow point excipient | $C_{10}$-$C_{18}$ Triglycerides (Gelucire ® 43/01) | 64.82 |
| Antioxidant | Rosemary Extract | 5.03 |
| High flow point excipient | Glyceryl behenate (Compritol ® E-ATO) | 15.08 |
| Dispersing agent | Lecithin | 5.03 |

Appropriate quantities of the low flow point excipient (Gelucire® 43/01), the high flow point excipient (Compritol® E-ATO), and the dispersing agent (lecithin) were melted in a water-jacketed tank at 70° C. After cooling the molten mixture to 65° C., the antioxidant (Rosemary Extract) was added and mixed with the molten mixture. The active (supplied as AstaREAL® Astaxanthin 10% oil) was then added to the molten mixture. The molten mixture was then directed to a melt-spray congeal apparatus equipped with a spinning disk atomizer at 1600 rpm. Droplets of the molten mixture formed and were congealed at about 4° C. using air, which flowed through the collection chamber at 130 SCFM. The resulting particles were collected.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A composition comprising a plurality lipid of particles that are solid at ambient temperature, have a generally spherical shape, and have a mean diameter ranging from 100 µm to 3000 µm, said lipid particles comprising at least one active agent, and a matrix, wherein said matrix comprises
   a) at least one low flow point excipient wherein the low flow point excipient has a melting point of less than 50° C., wherein the low flow point excipient consists of one or more of polyglycolized glycerides, a mixture of C10-C18 triglycerides, stearoyl polyoxylglycerides, lauroyl macrogol-32 glycerides, fatty acid esters of glycols, fatty acid esters of poly glycols, fatty acid esters of polyglycerols, myristyl alcohol, lauryl alcohol, capric alcohol, lauric acid, oleic acid, and mixtures thereof; and
   b) at least one high flow point excipient wherein the high flow point excipient has a melting point of 50° C. or greater;
   wherein a mass ratio of the at least one low flow point excipient and the at least one high flow point excipient is greater than 4:1.

2. The composition of claim 1 wherein a mass ratio of said at least one low flow point excipient and said at least one high flow point excipient is at least 10:1.

3. The composition of claim 1 wherein a mass ratio of said at least one low flow point excipient and said at least one high flow point excipient is at least 15:1.

4. The composition of claim 1 comprising from 1 wt % to 60 wt % of the active agent.

5. The composition of claim 1 wherein the high flow point excipient comprises at least 2 wt % of the composition.

6. The composition of claim 1 wherein the particles further comprise from 0.01 wt % to 20 wt % of a dispersing agent.

7. The composition of claim 1 wherein said particles further comprise from 0.01 wt % to 20 wt % of an antioxidant.

8. The composition of claim 1 wherein said composition further comprises 0.01 wt % to 5 wt % of a flow aid.

9. A composition comprising:
   a plurality of lipid particles that are solid at ambient temperature, have a mean diameter ranging from 100 µm to 3000 µm, said lipid particles comprising at least one active agent, and a matrix, wherein said matrix comprises
   a) at least one low flow point excipient, wherein the low flow point excipient consists of one or more of polyglycolized glycerides, a mixture of C10-C18 triglycerides, stearoyl polyoxylglycerides, lauroyl macrogol-32 glycerides, fatty acid esters of glycols, fatty acid esters of poly glycols, fatty acid esters of polyglycerols, myristyl alcohol, lauryl alcohol, capric alcohol, lauric acid, oleic acid, and mixtures thereof, and wherein the low flow point excipient has a melting point of less than 50° C.;
   b) at least one high flow point excipient, wherein the high flow point excipient has a melting point of 50° C. or greater; and
   wherein a mass ratio of the at least one low flow point excipient and the at least one high flow point excipient is greater than 4:1;
   wherein said composition has an in vivo AUC value, wherein the AUC value divided by the amount dosed is at least 1.25-fold compared to an AUC value of a control dosage form divided by the amount dosed.

10. The composition of claim 1 wherein said active agent is a carotenoid.

11. The composition of claim 10 wherein said carotenoid comprises lutein, astaxanthin, zeaxanthin, alpha-carotene, beta-carotene, cryptoxanthin, lycopene, and mixtures thereof.

12. The composition of claim 9 wherein the active agent is a carotenoid.

13. The composition of claim 12 wherein the carotenoid comprises lutein, astaxanthin, zeaxanthin, alpha-carotene, beta-carotene, cryptoxanthin, lycopene, and any mixture thereof.

14. The composition of claim 1 wherein the high flow point excipient comprises glycerol behenate, glycerol dibehenate, glycerol palmitate, hydrogenated castor oil, stearyl alcohol, behenyl alcohol, palmitic acid, stearic acid, paraffin wax, beeswax, candelilla wax, carnauba wax, and mixtures thereof.

* * * * *